United States Patent [19]

Tachizawa et al.

[11] Patent Number: 5,284,602
[45] Date of Patent: Feb. 8, 1994

[54] N-(N'-LONG CHAIN ACYL-$\beta$-ALANYL)-$\beta$-ALANINE OR ITS SALT AND DETERGENT COMPOSITION CONTAINING THE SAME

[75] Inventors: Osamu Tachizawa; Masayo Kawaguchi; Kohshiro Sotoya, all of Wakayama, Japan

[73] Assignee: Kao Corporation, Tokyo, Japan

[21] Appl. No.: 933,698

[22] Filed: Aug. 24, 1992

[30] Foreign Application Priority Data

Aug. 26, 1991 [JP] Japan .................................. 3-213808
Sep. 25, 1991 [JP] Japan .................................. 3-246162

[51] Int. Cl.$^5$ .......................... C11D 3/26; C07C 229/00
[52] U.S. Cl. ..................................... 252/546; 252/544; 252/DIG. 13; 554/77; 562/561
[58] Field of Search ............... 252/546, DIG. 13, 544; 554/37; 562/561

[56] References Cited

U.S. PATENT DOCUMENTS

| | | | |
|---|---|---|---|
| 2,880,178 | 3/1959 | Ruff et al. | 252/137 |
| 2,956,068 | 10/1960 | Dohr et al. | 260/404.5 |
| 4,749,515 | 6/1988 | Miyamoto et al. | 252/545 |
| 4,919,846 | 4/1990 | Nakama et al. | 252/542 |

FOREIGN PATENT DOCUMENTS

18319 6/1981 Hungary .
195046 11/1982 Japan .
026029 2/1983 Japan .
130866 6/1985 Japan .

OTHER PUBLICATIONS

Riso, Richard Protein Detergents Dec. 4, 1962 pp. 3–8.
Zussman, Acylated Amino Acids in Shampoos vol. 6 #5 Dec. 1955 pp. 407–415.
Maypons for Cosmetics, Nov. 1955 pp. 1–5.

*Primary Examiner*—Paul Lieberman
*Assistant Examiner*—Michael P. Tierney
*Attorney, Agent, or Firm*—Sughrue, Mion, Zinn, Macpeak & Seas

[57] ABSTRACT

An N-(N'-long chain acyl-$\beta$-alanyl)-$\beta$-alanine represented by formula (1):

$$R-(\overset{\overset{\displaystyle O}{\|}}{C}-NH-CH_2CH_2)_2COOM \qquad (1)$$

wherein R represents a straight-chain or branched-chain alkyl or alkenyl group having from 7 to 23 carbon atoms; and M represents a hydrogen atom, an alkali metal, an ammonium, an alkylammonium, an alkanolammonium or a basic amino acid;

or its salt and a detergent composition containing the same are disclosed.

The detergent composition of the present invention is excellent in foaming power and gives a good feel after washing.

4 Claims, No Drawings

N-(N'-LONG CHAIN ACYL-β-ALANYL)-β-ALANINE OR ITS SALT AND DETERGENT COMPOSITION CONTAINING THE SAME

FIELD OF THE INVENTION

This invention relates to a novel N-(N'-long chain acyl-β-alanyl)-β-alanine or its salt, and a detergent composition containing the same which has a high foaming power and gives a good feel after washing. More particularly, the present invention relates to a detergent composition for washing the hair or skin which shows sustained foaming and can be easily rinsed.

BACKGROUND OF THE INVENTION

In general, detergent compositions contain ordinary anionic surfactants as the main component together with higher fatty acids (in the case of skin cleansers) or higher alcohol sulfate salts or polyoxyethylene higher alcohol sulfate salts (in the case of hair shampoos). However, these ordinary surfactants have various disadvantages. For example, a detergent containing higher fatty acids frequently causes the formation of scum (calcium salts of higher fatty acids) upon rinsing. Further, such a detergent is insufficient in foaming power or sustained foaming. On the other hand, higher alcohol sulfate salts are poor in foam breakage or cannot give a smooth feel to the shampooed hair.

Inorganic or organic salts of N-long chain acyl amino acids, which are excellent not only in surface activity but also in bactericidal action, have been widely employed in recent years. It is known that detergents containing these components have a high detergency and exert mild actions on the skin. For example, JP-A-50-150701 and JP-A-63-2962 disclose low-irritative liquid detergents containing N-long chain acyl amino acid surfactants as basic ingredients while JP-A-53-132007 discloses an improved solid detergent containing an N-long chain acyl neutral amino acid (the term "JP-A" as used herein means an "unexamined published Japanese patent application").

Although the tertiary amide-type N-long chain acyl amino acid salts employed in the detergents disclosed in these patents are highly soluble in water, they are poor in foaming power and foam breakage. In addition, they give a slimy feel at the use.

On the other hand, a secondary amide-type N-long chain acyl amino acid salt is described as a low irritancy surfactant in an Example in JP-A-63-2962. According to this Example, however, satisfactory effects cannot be achieved thereby. Further, a detergent composition containing the secondary amide-type N-long chain acyl amino acid salt alone as a base scarcely shows a satisfactory foaming power or sustained foaming and gives a good feel at the use.

SUMMARY OF THE INVENTION

It is an object of the present invention to provide a novel detergent composition containing an N-long chain acyl amino acid derivative which has a sufficient foaming power and gives a good feel after washing.

As a result of extensive investigations to solve the above-mentioned problems, the present inventors successfully found that a detergent composition containing an N-(N'-long chain acyl-β-alanyl)-β-alanine represented by the following general formula (1) or its salt is excellent in foaming power and foam breakage, and gives a good feel after washing. These findings have now led to completion of the present invention.

Thus, the present invention provides an N-(N'-long chain acyl-β-alanyl)-β-alanine represented by formula (1):

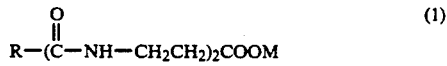

wherein R represents a straight-chain or branched-chain alkyl or alkenyl group having from 7 to 23 carbon atoms; and M represents a hydrogen atom, an alkali metal, an ammonium, an alkylammonium, an alkanolammonium or a basic amino acid;

or its salt and a detergent composition containing the same.

Further, the present inventors found that a detergent composition which comprises a combination of an N-(N'-long chain acyl-β-alanyl)-β-alanine represented by the above general formula (1) or its salt with an N-long chain acyl amino acid represented by formula (2):

wherein R and M are the same as defined in the above general formula (1);

at a specific ratio [i.e., comprising (a) an N-(N'-long chain acyl-β-alanyl)-β-alanine represented by the general formula (1) or its salt and (b) an N-long chain acyl amino acid represented by the general formula (2) at a weight ratio (a)/(b) of from 1/100 to 5/100] shows a good foaming and sustained foaming in washing, a good foam breakage in rinsing and gives a good feel after washing.

DETAILED DESCRIPTION OF THE INVENTION

Examples of the alkyl group represented by R in the N-(N'-long chain acyl-β-alanyl)-β-alanine of the general formula (1) (hereinafter, referred to as "the compound (1)") and the N-long chain acyl amino acid of the general formula (2) (hereinafter, referred to as "the compound (2)") include straight-chain or branched-chain heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl and tricosyl groups and examples of the alkenyl group include straight-chain or branched-chain heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl and tricosenyl groups.

Examples of the alkylammonium group represented by M in the compound (1) and the compound (2) include trimethyl-ammonium and triethylammonium, examples of alkanolammonium include monoethanolammonium, diethanolammonium and triethanolammonium, examples of the basic amino acid include lysine and arginine, and examples of the alkali metal include sodium and potassium.

The compound (1) may be produced by, for example, converting an N-long chain acyl-β-alanine into an acid halide with the use of a halogenation agent such as phosphorus trichloride, thionyl chloride or phosgene and then condensing the resulting acid halide with β- alanine, or converting an N-long chain acyl-β-alanine into an acid anhydride and then reacting the resulting acid anhydride with β-alanine.

The former method, via an acid halide, may be performed, for example, in the following manner. First, an N-long chain acyl-β-alanine is dispersed in a solvent and a halogenating agent 1 to 5 times equivalent with the N-long chain acyl-β-alanine is added thereto to thereby give an N-long chain acyl-3-aminopropionic acid halide.

Examples of the solvent to be used in the halogenation include methylene chloride, chloroform, carbon tetrachloride, benzene, toluene and xylene.

The N-long chain acyl-3-aminopropionic acid halide thus obtained is a straight-chain or branched-chain acid halide having from 8 to 24 carbon atoms which may be saturated or unsaturated. Examples thereof include acid halides consisting of a single component such as a N-lauroyl-3-aminopropionic acid halide, N-palmitoyl-3-aminopropionic acid halide and N-stearoyl-3-aminopropionic acid halide as well as mixed acid halides such as N-cocoyl-3-aminopropionic acid halide and N-tallowyl-3-aminopropionic acid halide. Examples of the halide include chlorides and bromides.

Next, β-alanine and an alkaline substance 0.8 to 2 times equivalent with the β-alanine are dissolved or dispersed in a solvent. Then, the above-mentioned N-long chain acyl-3-aminopropionic acid halide 0.3 to 1 time equivalent with the β-alanine is added thereto while maintaining the mixture at a temperature of from 5° to 50° C. and thus acylation is carried out to obtain the target compound (1).

Examples of the solvent to be used in this acylation include water, methanol, ethanol, isopropanol, n-butanol, t-butanol, acetone, tetrahydrofuran, ethyl acetate, toluene, DMF and DMSO. The solvent may be used either alone or as a combination of two or more. Further, an alkaline substance form 0.3 to 1 time equivalent with the β-alanine may be simultaneously added, if required, in this reaction.

Examples of the alkaline substance to be used here include sodium hydroxide and potassium hydroxide. The alkaline substance may be used either alone or as a combination of two or more.

It is preferable that the N-(N'-long chain acyl-β-alanyl)-β-alanine thus obtained is used in the form of sodium salt, potassium salt, ammonium salt, triethanolamine salt or a basic amino acid salt such as lysine salt.

The N-long chain acyl amino acid (b) represented by the above general formula (2) may be produced by Shotten-Baumann reaction wherein an alkali aqueous solution of an amino acid is reacted with a fatty acid halide or a modified method thereof wherein an amino acid aqueous solution containing a hydrophilic solvent is reacted with a fatty acid halide in the presence of an alkali (refer to JP-B-46-8685 (corresponding to U.S. Pat. No. 3,758,525) or JP-B-51-38681, the term "JP-B" as used herein means an "examined Japanese patent publication").

The total content of the N-(N'-long chain acyl-β-alanyl)-β-alanine (a) and the N-long chain acyl amino acid (b) in the detergent composition of the present invention may be 5% by weight or above and preferably ranges from 10 to 80% by weight. When the total content of these components is less than 5% by weight, a satisfactory feel cannot be obtained at the use.

The weight ratio of the compound (a) to the compound (b) may preferably range from 1/100 to 5/100.

When the weight ratio is less than 1/100 or exceeds 5/100, the resulting detergent composition tends to be poor in foam stability and the feel at the use.

The detergent composition of the present invention containing N-(N'-long chain acyl-β-alanyl)-β-alanine may be used as, for example, a kitchen cleaner, a hard-surface detergent, a shampoo, a face cleanser, a body cleanser or a bubble bath detergent, depending on the purpose. A detergent composition further containing the compound of the general formula (2) is suitable, in particular, for a shampoo, a face cleanser or a body cleanser. The detergent composition of the present invention may further contain various auxiliary components usually employed in the art (for example, perfumes, colorants, humectants, builders, hydrotrops, preservatives, etc.).

In order to control the foaming or the detergency, the detergent composition of the present invention may further contain various anionic surfactants, cationic surfactants, ampholytic surfactants or nonionic surfactants. Examples of these surfactants include fatty acid soaps, higher alcohol sulfate salts, polyoxyethylene higher alcohol sulfate salts, higher alcohol phosphates and salts thereof, polyoxyethylene higher phosphates and salts thereof, polyoxyethylene higher fatty acid phosphates and slats thereof, sulfonated higher fatty acid salts, sulfonated higher fatty acid alcohol ester salts, isethionic acid higher fatty acid ester salts, α-sulfo higher fatty acid ester salts, higher alkyldimethylbenzylammonium salts, higher alkylamines, higher alkyltrimethylammonium salts, higher fatty acid diethanolamides and ethylene oxide or propylene oxide adducts thereof, higher fatty acid monoethanolamides and ethylene oxide or propylene oxide adducts thereof, polyoxyethylene higher fatty acid monoethanolamide phosphates, N-long chain acyl amino acid salts such as N-long chain acyl acidic amino acid salts, N-long chain acyl sarcosine salts and N-long chain acyl-β-alanine salts, higher alkyl aminopropionates such as lauryl aminopropionates, higher alkyl iminodiacetates such as lauryl iminodiacetate, and amine amide compounds such as higher alkyl dimethylbetaine, higher alkyl dihydroxyethylbetaine, N-alkyloyl-N'-(2-hydroxyethyl)-N'-carboxymethylethylenediamine salts and N-alkyloyl-N-(2-hydroxyethyl)-N',N'-biscarboxy-methylethylenediamine, though the present invention is not restricted thereto.

The content of the N-(N'-long chain acyl-β-alanyl)-β-alanine or its salt of the present invention in the detergent composition may be optionally selected depending on the purpose. In general, the detergent composition usually contains from 0.01 to 90% by weight (preferably 0.01 to 50% by weight) of the above compound or its salt.

The detergent composition of the present invention is superior in foaming power, sustained foaming and foam breakage to conventional detergents comprising higher fatty acid alkali salts, higher alcohol sulfate salts or polyoxyethylene higher alcohol sulfate salts as the main component. In addition, it gives an excellent feel at the use, without showing any unsmoothness or slimy feel different from conventional products The present invention is further illustrated in greater detail by the following Examples, but the present invention is not limited thereto.

EXAMPLE 1

Production of N-(N'-lauroyl-β-alanyl)-β-alanine:

(1) Halogenation 46.8 g of N-lauroyl-β-alanine was dispersed in 155 ml of methylene chloride. Then, 24.8 g of thionyl chloride was added thereto within 10 minutes under stirring while maintaining the temperature of the mixture at 20° C. After the completion of the addition, the mixture was stirred at the same temperature for 30 minutes so as to complete the reaction. When the reaction solution thus obtained was analyzed by infrared spectroscopy, a peak at 1695 cm$^{-1}$ due to carboxylic acid (—COOH) disappeared while a new peak due to acid chloride (—COCl) was formed at 1782 cm$^{-1}$. These facts indicated that an acid chloride was obtained. Then, the methylene chloride employed as the solvent and side products (sulfur dioxide and hydrogen chloride) were distilled off from the reaction mixture under reduced pressure. Thus, 50.5 g of N-lauroyl-3-aminopropionic acid chloride was obtained.

(2) Acylation 17.1 g of β-alanine and 10.6 g of potassium hydroxide were dissolved in 90 ml of water. To the obtained solution, 50.5 g of N-lauroyl-3-aminopropionic acid chloride obtained in the above (1), dissolved in 130 ml of tetrahydrofuran, and 32.7 g of a 30% aqueous solution of potassium hydroxide were added dropwise within 1 hour. During this addition stage, the reaction mixture was stirred and the temperature and pH value of the reaction mixture were maintained respectively at 20° to 25° C. and from 11 to 13.

After the completion of the addition, the mixture was stirred at the same temperature for additional 1 hour so as to complete the acylation. Next, 6N hydrochloric acid was added to the reaction mixture under stirring until the pH value of the mixture reached 1. Then, the obtained mixture was further stirred for 1 hour. The crystals thus precipitated were collected by filtering, and then dried at 50° C./100 mmHg. Thus, 55 g of the target compound was obtained.

The IR spectrum and NMR spectrum of the crystals thus obtained proved that the product had the following structure.

$$C_{11}H_{23}\overset{O}{\underset{\|}{C}}NHC_2H_4\overset{O}{\underset{\|}{C}}NHC_2H_4COOH$$

NMR spectrum (DMSO-d$_6$, internal standard TMS): 2.0 ppm (t, 2H), 2.25 ppm (t, 2H), —CH$_2$CONH— 2.4 ppm (t, 2H), —CH$_2$COOH 3.2-3.4 ppm (m, 4H) —CONHCH$_2$—7.75 ppm (t, 1H), 7.9 ppm (t, 1H) —CONH—.

IR spectrum (KBr tablet): 1720 cm$^{-1}$, 1655 cm$^{-1}$, 1565 cm$^{-1}$.

EXAMPLE 2

Production of N-(N'-cocoyl-β-alanyl)-β-alanine:

(1) Halogenation 46.6 g of N-cocoyl-β-alanine was dispersed in 155 ml of methylene chloride. Then, 24.8 g of thionyl chloride was added thereto within 10 minutes under stirring while maintaining the temperature of the mixture at 20° C. After the completion of the addition, the mixture was stirred at the same temperature for 30 minutes so as to complete the reaction. When the reaction solution thus obtained was analyzed by infrared spectroscopy, a peak at 1695 cm$^{-1}$ due to carboxylic acid (—COOH) disappeared while a new peak due to acid chloride (—COCl) was formed at 1785 cm$^{-1}$. These facts indicated that an acid chloride was obtained. Then, the methylene chloride employed as the solvent and side products (sulfur dioxide and hydrogen chloride) were distilled off from the reaction mixture under reduced pressure. Thus, 50.0 g of N-cocoyl-3-aminopropionic acid chloride was obtained.

(2) Acylation 17.1 g of β-alanine and 10.6 g of potassium hydroxide were dissolved in 90 ml of water. To the obtained solution, 49.0 g of N-cocoyl-3-aminopropionic acid chloride obtained in the above (1), dissolved in 130 ml of tetrahydrofuran, and 32.7 g of a 30% aqueous solution of potassium hydroxide were added dropwise within 1 hour. During this addition stage, the reaction mixture was stirred and the temperature and pH value of the reaction mixture were maintained respectively at 20° to 25° C. and from 11 to 13.

After the completion of the addition, the mixture was stirred at the same temperature for additional 1 hour so as to complete the acylation. Next, 6N hydrochloric acid was added to the reaction mixture under stirring until the pH value of the mixture reached 1. Then, the obtained mixture was further stirred for 1 hour. The crystals thus precipitated were collected by filtering, and then dried at 50° C./100 mmHg. Thus, 53.5 g of the target compound was obtained.

The IR spectrum and NMR spectrum of the crystals thus obtained proved that the product had the following structure.

$$R'CH_2\overset{O}{\underset{\|}{C}}NHC_2H_4\overset{O}{\underset{\|}{C}}NHC_2H_4COOH$$

wherein $$R'CH_2\overset{O}{\underset{\|}{C}}-$$

represents an acyl group originating from coconut oil fatty acids.

NMR spectrum (DMSO-d$_6$, internal standard TMS): 2.1 ppm (t, 2H), 2.3 ppm (t, 2H), —CH$_2$CONH— 2.4 ppm (t, 2H), —CH$_2$COOH 3.1-3.4 ppm (m, 4H) —CONHCH$_2$— 7.7 ppm (t, 1H), 7.9 ppm (t, 1H) -CONH—.

IR spectrum (KBr tablet): 725 cm$^{-1}$, 1645 cm$^{-1}$, 1550 cm$^{-1}$.

EXAMPLE 3

Production of N-(N'-oleoyl-β-alanyl)-β-alanine:

(1) Halogenation 61.3 g of N-oleoyl-β-alanine was dispersed in 200 ml of methylene chloride. Then, 24.8 g of thionyl chloride was added thereto within 10 minutes under stirring while maintaining the temperature of the mixture at 20° C. After the completion of the addition, the mixture was stirred at the same temperature for 30 minutes so as to complete the reaction. When the reaction solution thus obtained was analyzed by infrared spectroscopy, a peak at 1695 cm$^{-1}$ due to carboxylic acid (—COOH) disappeared while a new peak due to acid chloride (—COCl) was formed at 1782 cm$^{-1}$. These facts indicated that an acid chloride was obtained. Then, the methylene chloride employed as the solvent and side products (sulfur dioxide and hydrogen chloride) were distilled off from the reaction mixture under reduced pressure. Thus, 64.1 g of N-oleoyl-3-aminopropionic acid chloride was obtained.

(2) Acylation 17.1 g of β-alanine and 10.6 g of potassium hydroxide were dissolved in 120 ml of water. To the obtained solution, 64.1 g of N-oleoyl-3-aminopropionic acid chloride obtained in the above (1), dissolved in 150 ml of tetrahydrofuran, and 32.7 g of a 30% aqueous solution of potassium hydroxide were added dropwise within 1 hour. During this addition stage, the reaction mixture was stirred and the temperature and pH value of the reaction mixture were maintained respectively at 20° to 25° C. and from 11 to 13.

After the completion of the addition, the mixture was stirred at the same temperature for additional 1 hour so as to complete the acylation. Next, 6N hydrochloric acid was added to the reaction mixture under stirring until the pH value of the mixture reached 1. Then, the obtained mixture was further stirred for 1 hour. The crystals thus precipitated were collected by filtering, and then dried at 50° C./100 mmHg. Thus, 68 g of the target compound was obtained.

The IR spectrum and NMR spectrum of the crystals thus obtained proved that the product had the following structure.

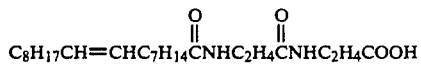

NMR spectrum (DMSO-$d_6$, internal standard TMS): 2.1 ppm (t, 2H), 2.3 ppm (t, 2H), —$CH_2CONH$— 2.4 ppm (t, 2H), —$CH_2COOH$ 3.2-3.4 ppm (m, 4H) —$CONHCH_2$— 5.3-5.4 ppm (m, 2H) —$C\underline{H}=C\underline{H}$— 7.8 ppm (t, 1H), 7.9 ppm (t, 1H) —$CON\underline{H}$—.

IR spectrum (KBr tablet): 1720 $cm^{-1}$, 1650 $cm^{-1}$, 1560 $cm^{-1}$.

EXAMPLE 4

By using the compounds of the present invention obtained in the above Examples 1 to 3 and N-lauroyl-N-methyl-β-alanine, which was employed for comparison, detergent compositions 1 to 4 as specified below were produced. Then, the foaming power, foam breakage upon rinsing, smoothness, smoothness after rinsing and smoothness after drying of each case where examined. The results are shown in Table 1 below.

Test method

Measurement of foam volume:

Each detergent composition was diluted 20-fold with water and 100 ml of the solution thus obtained (solution temperature: 40° C.) was poured into a graduated cylinder. Then, mixing blades were provided in the above-mentioned solution. 30 seconds after the initiation of mixing, the volume (ml) of the foam thus formed was measured and referred to as the foam volume. The mixing blades were stirred at a speed of 1,000 r.p.m. and the rotation was reversed at intervals of 5 seconds.

Evaluation of feet at the use:

A sensory evaluation was carried out by employing 10 male and female panelists (5 males and 5 females) who washed the hair and skin with each detergent composition. The evaluation was made based on the following criteria. The average of the scores was calculated for each evaluation item and a score of 4.5 or above was regarded as very good (⊙), that of 3.5 to 4.4 was regarded as good (), that of 2.5 to 3.4 was regarded as moderate (Δ) and that of 2.4 or below was regarded as poor (x).

(1) Foam breakage in rinsing:
5: Very good.
4: Good.
3: Moderate.
2: Poor.
1: Very poor.

(2) Smoothness in rinsing, (3) Smoothness after rinsing and (4) Smoothness after drying:
5: Very good.
4: Good.
3: Moderate.
2: Poor.
1: Very poor.

|  | (% by weight) |
|---|---|
| Composition 1 (invention product): | |
| (1) N-(N'-lauroyl-β-alanyl)-β-alanine | 30 |
| (2) lauric acid TEA salt | 5 |
| (3) lauryldimetylamine oxide | 2 |
| (4) perfume | 0.5 |
| (5) dibutylhydroxytoluene | 0.2 |
| (6) ethanol | 3 |
| (7) water | the balance. |
| Composition 2 (invention product): | |
| (1) N-(N'-cocoyl-β-alanyl)-β-alanine | 30 |
| (2) lauric acid TEA salt | 5 |
| (3) lauryldimetylamine oxide | 2 |
| (4) perfume | 0.5 |
| (5) dibutylhydroxytoluene | 0.2 |
| (6) ethanol | 3 |
| (7) water | the balance. |
| Composition 3 (invention product): | |
| (1) N-(N'-oleoyl-β-alanyl)-β-alanine | 30 |
| (2) lauric acid TEA salt | 5 |
| (3) lauryldimetylamine oxide | 2 |
| (4) perfume | 0.5 |
| (5) dibutylhydroxytoluene | 0.2 |
| (6) ethanol | 3 |
| (7) water | the balance. |

Composition 4 (comparative product):

(N-lauroyl-N-methyl-β-alanine, which had been hitherto employed as a low-irritative surfactant and had a structure similar to the compound of the present invention, was used as a comparative product)

|  | (% by weight) |
|---|---|
| (1) N-lauroyl-N-methyl-β-alanine | 30 |
| (2) lauric acid TEA salt | 5 |
| (3) lauryldimetylamine oxide | 2 |
| (4) perfume | 0.5 |
| (5) dibutylhydroxytoluene | 0.2 |
| (6) ethanol | 3 |
| (7) water | the balance. |

TABLE 1

| | Composition No. | | | |
| | Invention | | | Comparison |
| | 1 | 2 | 3 | 4 |
|---|---|---|---|---|
| Foam volume (ml) | 220 | 210 | 200 | 160 |
| Feel at the use: | | | | |
| Foam breakage in rinsing | ⊙ | ⊙ | ⊙ | x |
| Smoothness in rinsing | ⊙ | ⊙ | ⊙ | Δ |
| Smoothness after rinsing | ○ | ○ | ○ | x |
| Smoothness after | ○ | ○ | ○ | Δ |

| | Composition No. | | | |
|---|---|---|---|---|
| | Invention | | | Comparison |
| | 1 | 2 | 3 | 4 |
| drying | | | | |

From the results shown in Table 1, it can be seen that a detergent composition containing the N-(N'-long chain acyl-β-alanyl)-β-alanine of the present invention as the main component is excellent in foaming power and gives a good feel at the use.

EXAMPLE 4

The foam volume, foam breakage and feel at the use of each of the following detergent compositions 5 to 8 according to the present invention and the following detergent compositions 9 to 11 employed for comparison were evaluated by the methods as specified below. The results are shown in Table 2 below.

Measurement of foam volume:

The procedure described in the above Example 4 was repeated except that the volume of foam remaining 2 minutes after stopping the mixing was further measured as an indicator for the sustained foaming.

Evaluation of feel at the use:

The procedure described in the above Example 4 was repeated.

| | (% by weight) |
|---|---|
| Composition 5 (invention product): | |
| (1) N-lauroyl-β-alanine triethanolamine salt (hereinafter, triethanolamine will be merely referred to as "TEA") | 30 |
| (2) N-(N'-lauroyl-β-alanyl)-β-alanine TEA salt | 0.6 |
| (3) lauric acid TEA salt | 5 |
| (4) lauryldimethylamine oxide | 2 |
| (5) perfume | 0.5 |
| (6) dibutylhydroxytoluene | 0.2 |
| (7) ethanol | 3 |
| (8) water | the balance. |
| Composition 6 (invention product): | |
| (1) N-cocoyl-β-alanine TEA salt | 30 |
| (2) N-(N'-cocoyl-β-alanyl)-β-alanine TEA salt | 0.6 |
| (3) lauric acid TEA salt | 5 |
| (4) lauryldimethylamine oxide | 2 |
| (5) perfume | 0.5 |
| (6) dibutylhydroxytoluene | 0.2 |
| (7) ethanol | 3 |
| (8) water | the balance. |
| Composition 7 (invention product): | |
| (1) N-lauroyl-β-alanine TEA salt | 30 |
| (2) N-(N'-lauroyl-β-alanyl)-β-alanine TEA salt | 1.5 |
| (3) alkyl polyglucoside (C12, degree of condensation: G 1.4) | 5 |
| (4) lauryldimethylamine oxide | 2 |
| (5) perfume | 0.5 |
| (6) dibutylhydroxytoluene | 0.2 |
| (7) ethanol | 3 |
| (8) water | the balance. |
| Composition 8 (invention product): | |
| (1) N-oleoyl-β-alanine TEA salt | 30 |
| (2) N-(N'-oleoyl-β-alanyl)-β-alanine TEA salt | 0.6 |
| (3) lauric acid TEA salt | 5 |
| (4) lauryldimethylamine oxide | 2 |
| (5) perfume | 0.5 |
| (6) dibutylhydroxytoluene | 0.2 |
| (7) ethanol | 3 |
| (8) water | the balance. |
| Composition 9 (comparative product): | |
| (1) N-lauroyl-β-alanine TEA salt | 30 |
| (2) lauric acid TEA salt | 5 |
| (3) lauryldimethylamine oxide | 2 |
| (4) perfume | 0.5 |
| (5) dibutylhydroxytoluene | 0.2 |
| (6) ethanol | 3 |
| (7) water | the balance. |
| Composition 10 (comparative product): | |
| (1) N-lauroylglycine TEA salt | 30 |
| (2) lauric acid TEA salt | 5 |
| (3) lauryldimethylamine oxide | 2 |
| (4) perfume | 0.5 |
| (5) dibutylhydroxytoluene | 0.2 |
| (6) ethanol | 3 |
| (7) water | the balance. |
| Composition 11 (comparative product): | |
| (1) N-lauroyl-N-methyl-β-alanine TEA salt | 30 |
| (2) lauric acid TEA salt | 5 |
| (3) lauryldimethylamine oxide | 2 |
| (4) perfume | 0.5 |
| (5) dibutylhydroxytoluene | 0.2 |
| (6) ethanol | 3 |
| (7) water | the balance. |

TABLE 2

| | Composition No. | | | | | | |
|---|---|---|---|---|---|---|---|
| | Invention | | | | Comparison | | |
| | 5 | 6 | 7 | 8 | 9 | 10 | 11 |
| Foam volume (ml): | | | | | | | |
| Immediately | 240 | 220 | 235 | 200 | 220 | 200 | 160 |
| After 2 min. | 225 | 210 | 225 | 205 | 160 | 150 | 125 |
| (foaming stability) | | | | | | | |
| Feel at the use: | | | | | | | |
| Foam breakage in rinsing | ⊙ | ⊙ | ⊙ | ⊙ | ○ | ○ | x |
| Smoothness in rinsing | ⊙ | ⊙ | ⊙ | ⊙ | ○ | ○ | Δ |
| Smoothness after rinsing | ○ | ○ | ○ | ○ | Δ | Δ | x |
| Smoothness after drying | ○ | ○ | ○ | ○ | Δ | Δ | Δ |

From the results shown in Table 2, it can be seen that the detergent composition according to the present invention is excellent in foaming power, foaming stability and foam breakage, and gives a good feel at the use without showing any unsmoothness or slimy feel, different from conventional products.

When used in washing the hair or skin, the detergent composition of the present invention shows excellent foaming power and foaming stability. Further, it is excellent in the feel at the use (for example, foam breakage in rinsing, smoothness in rinsing, smoothness after rinsing, smoothness after drying) and never gives any unsmoothness or slimy feel which are often observed in the case of conventional products.

While the invention has been described in detail and with reference to specific embodiments thereof, it will be apparent to one skilled in the art that various changes and modifications can be made therein without departing from the spirit and scope thereof.

What is claimed is:

1. An N-(N'-long chain acyl-β-alanyl)-β-alanine or its salt represented by formula (1):

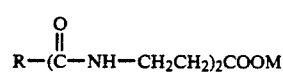

$$R-(\overset{O}{\underset{\|}{C}}-NH-CH_2CH_2)_2COOM \quad (1)$$

wherein R represents a straight-chain or branched-chain alkyl or alkenyl group having from 7 to 23 carbon atoms; and M represents a hydrogen atom, an alkali metal, an ammonium, an alkylammonium, an alkanolammonium or a basic amino acid.

2. A detergent composition comprising the following components (a) and (b) in a (a)/(b) weight ratio within the range of from 1/100 to 5/100:

(a) an N-(N'-long chain acyl-β-alanyl)-β-alanine or its salt represented by formula (1) as claimed in claim 1; and (b) an N-long chain acyl amino acid represented by formula (2)

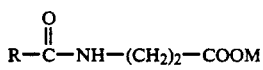 (2)

wherein R and M are the same as defined in claim 1.

(a) an N-(N'-long chain acyl-β-alanyl)-β-alanine represented by formula (1) or its salt as claimed in claim 1; and (b) an N-long chain acyl amino acid represented by formula (2):

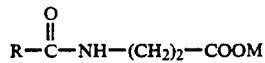 (2)

wherein R and M are the same as defined in claim 1.

3. The detergent composition as claimed in claim 2, wherein the total content of the component (a) and the component (b) is 5% by weight or more.

4. The detergent composition as claimed in claim 3, wherein the total content ranges from 10 to 80% by weight.

* * * * *